United States Patent
Sugiyama et al.

(10) Patent No.: US 8,361,390 B2
(45) Date of Patent: Jan. 29, 2013

(54) LIQUID CHROMATOGRAPH

(75) Inventors: Koji Sugiyama, Kyoto (JP); Toshikatsu Sakai, Kyoto (JP); Yoshikiyo Hongo, Koka (JP); Akira Sezaki, Kyoto (JP); Takanori Kamada, Kyoto (JP)

(73) Assignee: Arkray, Inc., Kyoto (JP)

( * ) Notice: Subject to any disclaimer, the term of this patent is extended or adjusted under 35 U.S.C. 154(b) by 803 days.

(21) Appl. No.: 12/223,814

(22) PCT Filed: Feb. 8, 2007

(86) PCT No.: PCT/JP2007/052269
§ 371 (c)(1),
(2), (4) Date: May 19, 2009

(87) PCT Pub. No.: WO2007/091654
PCT Pub. Date: Aug. 16, 2007

(65) Prior Publication Data
US 2009/0275119 A1    Nov. 5, 2009

(30) Foreign Application Priority Data

Feb. 9, 2006   (JP) .................................. 2006-032123

(51) Int. Cl.
*G01N 30/28* (2006.01)
*G01N 30/30* (2006.01)
*G01N 30/34* (2006.01)

(52) U.S. Cl. ..... 422/70; 73/61.56; 73/61.57; 210/198.2; 436/66; 436/67; 436/161

(58) Field of Classification Search ................... 422/70; 436/161, 66–67; 210/198.2, 656; 73/61.52–61.58
See application file for complete search history.

(56) References Cited

U.S. PATENT DOCUMENTS

| | | | |
|---|---|---|---|
| 3,779,708 A | 12/1973 | Runck et al. | |
| 4,013,417 A | 3/1977 | Raffaele | |
| 5,518,893 A | 5/1996 | Park et al. | |
| 5,693,122 A * | 12/1997 | Berndt | .............................. 96/6 |
| 6,319,398 B1 * | 11/2001 | Saitoh | ....................... 210/198.2 |

(Continued)

FOREIGN PATENT DOCUMENTS

| | | |
|---|---|---|
| EP | 0489569 A2 | 6/1992 |
| EP | 0 973 031 | 7/1998 |

(Continued)

OTHER PUBLICATIONS

Extended European search report from European Patent Office for application No. 10165796.3 dated May 4, 2011.

(Continued)

*Primary Examiner* — Jan Ludlow
(74) *Attorney, Agent, or Firm* — Rader, Fishman & Grauer PLLC

(57) ABSTRACT

The present invention relates to a liquid chromatography apparatus X, which is provided with a deaerator 4. The liquid chromatography apparatus X is further provided with a dissolved oxygen density adjusting means for maintaining a density of dissolved oxygen in an eluting solution to be supplied to a column 60 constant. Preferably, the dissolved oxygen density adjusting means is configured so as to adjust the density of the dissolved oxygen in the eluting solution by adjusting a degree of decompression in a decompression space of the deaerator 4 based on a measurement result by temperature measurement means 40A, 40B, and 40C for measuring the temperature of the eluting solution.

27 Claims, 13 Drawing Sheets

U.S. PATENT DOCUMENTS

| | | | |
|---|---|---|---|
| 6,322,752 B1 * | 11/2001 | Siddiqui et al. | 422/510 |
| 7,947,112 B1 * | 5/2011 | Gerner et al. | 95/46 |
| 2008/0006578 A1 * | 1/2008 | Sims et al. | 210/639 |

FOREIGN PATENT DOCUMENTS

| | | |
|---|---|---|
| EP | 2 017 615 | 1/2009 |
| JP | 60-255120 A * | 12/1985 |
| JP | 06-87870 U | 12/1994 |
| JP | 07-260545 A | 10/1995 |
| JP | 2001-108506 A | 4/2001 |
| JP | 2007-315816 | 12/2007 |
| WO | WO-96/40782 | 12/1996 |
| WO | WO-98/23939 | 6/1998 |

OTHER PUBLICATIONS

First Office Action from State Intellectual Property Office of People's Republic of China for application No. 200780012752.8 dated Aug. 18, 2011.

Office Action in Japanese Application No. 2007-557895, mailed Oct. 2, 2012.

* cited by examiner

LIQUID CHROMATOGRAPH

TECHNICAL FIELD

The present invention relates to a liquid chromatography apparatus, which can reduce an influence of dissolved oxygen in an eluting solution to be introduced into a column.

BACKGROUND ART

In the case of separating and analyzing a biogenic substance by using a biologic sample such as blood, a high-performance liquid chromatography apparatus (HPLC apparatus) by utilizing a high-performance liquid chromatography (HPLC) has been widely used (for example, refer to Patent Document 1). As shown in FIG. 12, a general HPLC apparatus is configured in such a manner that, adjusting a sample containing a biogenic substance in a sample adjustment unit 91, then, introducing the sample into an analysis column 90, the biogenic substance is absorbed into a column packing of the analysis column 90. On the other hand, the biogenic substance absorbed in the column packing is separated by supplying an eluting solution from an eluting solution bottle 93 to the analysis column 90 by means of a solution sending pump 92. The separated liquid from the analysis column 90 is introduced into a photometric mechanism 94, and by continuously measuring an absorbance of the separated liquid in the photometric mechanism 94, the analysis of the biogenic substance is carried out.

On the other hand, in order to stably carry out the separation analysis, in an HPLC apparatus 9, a deaerator 93 is mounted at the upstream of the solution sending pump 92 (for example, refer to Patent Document 2). The deaerator 93 serves to remove gas such as oxygen remaining in the eluting solution. By mounting this deaerator 93, it is possible to prevent gas dissolved in the eluting solution from being made into air bubbles and to prevent a feed rate of the solution sending pump 92 from being unstable. Therefore, it is possible to stably carry out the separation analysis in the HPLC apparatus 9.

As shown in FIG. 13, as a deaerator 95, there exists one that is configured so as to absorb and remove the dissolved gas in the eluting solution by distributing the eluting solution in a gas permeable tube 97 which is arranged in a decompression space 96, and decompressing the decompression space 96 by means of a pump 98 (for example, refer to Patent Document 3). In other words, the dissolved gas in the eluting solution is moved to the outside of the gas permeable tube 97 (the decompression space 96) when the eluting solution is distributed through the inside of the gas permeable tube 97, to be removed.

[Patent Document 1] Japanese Patent Application Laid-Open No. 7-120447
[Patent Document 2] Japanese Patent Application Laid-Open No. 2001-13345
[Patent Document 3] Japanese Patent Application Laid-Open No. 2000-275229

DISCLOSURE OF THE INVENTION

Problems to be Solved by the Invention

However, an amount of dissolution of the gas into the eluting solution is different depending on a temperature of the eluting solution, so that, in a case that a temperature of the outside of the apparatus (an environmental temperature) is varied, or in a case that the biogenic substance is analyzed with the environmental temperature being different, the state of the dissolved gas in the eluting solution becomes different. On the other hand, in the deaerator 93, regardless of the state of the dissolved gas in the eluting solution, a decompression degree in the decompression space 94 is made constant, and a detention time (a feed rate) of the eluting solution in the decompression space 94 is also made constant. Therefore, in the deaerator 93, regardless of the state of the dissolved gas in the eluting solution, only a constant amount of gas can be removed, so that in a case that an amount of the dissolved gas in the eluting solution is varied depending on variation of the environmental temperature or the like, the amount of the dissolved gas in the eluting solution to be supplied to the analysis column 90 is varied. As a result, in a case that an analysis is carried out under an environment that the environmental temperature varies largely, the analysis result is not stable, and in a case that an analysis is carried out under the environments that the environmental temperatures are different, the analysis result under each environment is different.

In addition, in a case of measuring density of glycohemoglobin in the blood sample, the glycohemoglobin is compassed as a rate of glycohemoglobin in the total amount of hemoglobin. However, in a case that the dissolved oxygen in the eluting solution is varied in accordance with variation of the environmental temperature or the like, a ratio between oxyhemoglobin and deoxyhemoglobin in the hemoglobin is varied. On the other hand, in the photometric mechanism 94, diluting the blood sample, the diluted blood sample is introduced into the analysis column 90 with oxygen being relatively affluent, so that 415 nm, which is the longest absorption wavelength of the oxyhemoglobin is used as a measurement wavelength. Therefore, under an environment where change of the environmental temperature is large, a ratio between oxyhemoglobin and deoxyhemoglobin is varied, so that it becomes difficult to accurately measure the density of glycohemoglobin due to the longest absorption wavelength of oxyhemoglobin.

Means for Solving the Problem

An object of the present invention is to appropriately prevent an influence to be given to an analysis result by dissolved oxygen in an eluting solution.

A first aspect of the present invention may provide a liquid chromatography apparatus provided with: a column holding a column package; and one or plural eluting solution holding parts holding the eluting solution to be supplied to the column; in which the liquid chromatography apparatus is further provided with a dissolved oxygen density adjusting means for maintaining a density of a dissolved oxygen in the eluting solution to be supplied to the column constant.

The liquid chromatography apparatus according to the present invention may be further provided with a deaerator for deaerating the eluting solution during supply of the eluting solution from the eluting solution holding part to the column, for example, and having a gas permeable film and a decompression space. In this case, it is preferable that the dissolved oxygen density adjusting means has a temperature measuring means for directly or indirectly measuring the temperature of the eluting solution to be supplied to the column, for example, and is configured so as to adjust a density of a dissolved oxygen in the eluting solution by adjusting a degree of decompression in the decompression space based on the measurement result by the temperature measuring means.

The liquid chromatography apparatus according to the present invention may be further provided with a first pipe for connecting between the eluting solution holding part and the deaerator; and a second pipe for connecting between the deaerator and the column. In this case, the temperature measuring means is configured so as to measure the temperatures of the eluting solutions filled in the first pipe, in the second pipe, or in the deaerator, or a temperature in the decompression space. In this case, it is assumed that the temperature measuring means has a thermistor, which is mounted inside of the first pipe, the second pipe, or in the deaerator.

The temperature measuring means may be also configured so as to measure an environmental temperature around the liquid chromatography apparatus or a temperature in the inside of the liquid chromatography apparatus. Here, the environmental temperature is any one of a peripheral temperature of the apparatus, a temperature of an exterior wall of the apparatus, or a temperature of the eluting solution holding part.

The liquid chromatography apparatus according to the present invention may be configured as one provided with a dissolved oxygen density measuring means for measuring a density of dissolved oxygen in an eluting solution filled in the pipe in place of a temperature measuring means. In this case, it is preferable that the dissolved oxygen density adjusting means is configured so as to adjust a density of dissolved oxygen in the eluting solution by adjusting a degree of decompression in the decompression space based on the measurement result by the dissolved oxygen density measuring means. For example, it is assumed that the dissolved oxygen density measuring means includes an oxygen sensor for measuring a density of oxygen of the eluting solutions in the first pipe, the second pipe, or the deaerator.

It is assumed that the deaerator is further provided with a pump for decompressing a decompression space, for example. In this case, it is preferable that the dissolved oxygen density adjusting means is configured so as to control an absorption power by controlling driving of the pump (for example, a driving voltage or an open state of a valve) and adjust a degree of decompression of a decompressed space.

The dissolved oxygen density adjusting means may be configured so as to have a temperature adjusting mechanism for heating or cooling the eluting solution. In this case, the temperature adjusting mechanism is configured so as to adjust the temperature of the eluting solution when the eluting solution passes through the first pipe, the second pipe, or the deaerator. In addition, the temperature adjusting mechanism may be also configured so as to adjust the temperature of the eluting solution based on the measurement result by the temperature measuring means for directly or indirectly measuring the temperature of the eluting solution to be supplied to the column.

The liquid chromatography apparatus according to the present invention may be configured so as to be further provided with an oxygen partial pressure variation control means for controlling variation of the oxygen partial pressure in the decompression space of the deaerator.

It is preferable that a pipe for supplying the eluting solution from the eluting solution holding part to the column has a poor oxygen permeable part, which is formed by a material having low oxygen permeability. In this case, the poor oxygen permeable part is provided in the entireness or a part of the second pipe for connecting between the deaerator and the column, for example.

It is assumed that the liquid chromatography apparatus according to the present invention includes a column, for example, and is further provided with an analysis unit, of which temperature is adjusted to be constant. In this case, it is preferable that the poor oxygen permeable part is provided at least in the part extended out from the analysis unit in the second pipe.

It is assumed that the analysis unit is further provided with a manifold, which is mounted in the mid of the second pipe, and in this case, it is preferable that the poor oxygen permeable part is mounted between the deaerator and the manifold in the second pipe.

It is assumed that the liquid chromatography apparatus according to the present invention is further provided with a detection mechanism for detecting a specific component in a sample based on the separated liquid from the column and an additional pipe for connecting between the column and the detection mechanism. In this case, it is preferable that the additional pipe has the poor oxygen permeable part, which is formed by a material having low oxygen permeability.

The poor oxygen permeable part is formed by nylon, polyether ether ketone (PEEK), polyethylene or stainless-steel (SUS), for example.

The liquid chromatography apparatus according to the present invention may be further provided with a sample adjusting means for adjusting a sample to be introduced into the column. The sample adjusting means dilutes a sample containing a red blood cell after hemolyzing the red blood cell by using a dilute solution, and is configured so that a degree of oxygen saturation in the sample becomes 85% or more by leaving the diluted sample for a predetermined time.

The sample adjusting means is configured so as to use a solution having a high degree of oxygen saturation as the dilute solution, for example, and leave the sample for a predetermined time after dilution. It is preferable that the time for leaving the sample after dilution is one minute or more. It is preferable that, as a dilute solution, a solution, of which degree of oxygen saturation is 85% or more, is used.

The sample adjusting means may be also configured so that a degree of oxygen saturation in the sample becomes 85% or more by opening the diluted sample to air for a predetermined time. It is assumed that, in this case, a time for opening the sample to air is one minute or more, for example, and preferably, one to two minutes.

The sample adjusting means may be also configured so that a degree of oxygen saturation in the sample becomes 85% or more by bubbling the sample by using air or oxygen-rich gas.

The sample adjusting means is configured so as to collect a sample for adjustment from an upper layer part of a layer containing many blood cells in the sample containing a blood cell. The sample adjusting means is configured so as to collect a sample for adjustment from an upper layer part of a blood cell layer when separating the blood sample containing blood cells into a red blood cell-rich blood cell layer and a red blood cell-poor blood plasma layer, and to adjust a sample for introduction to be introduced into the column by using the sample for adjustment. In this case, the sample adjusting means is provided with a detecting means for detecting an interface between the blood cell layer and the blood plasma layer; and a sampling nozzle for collecting the sample for adjustment from the upper layer part of the blood cell layer, for example.

The sampling noise is operated so as to collect the sample for adjustment from the upper layer part of the blood cell layer based on a detection result by the detecting means, for example, from an area, of which distance from the upper interface of the blood cell layer is in the range of 5 to 30% to a thickness of the blood cell layer, or an area, of which distance from the upper interface of the blood cell layer is in the range of 0.5 to 5.0 mm.

The liquid chromatography apparatus according to the present invention is configured so as to measure glycohemoglobin in a sample, for example.

A second aspect of the present invention may provide a liquid chromatography apparatus, which is configured so as to measure glycohemoglobin in a sample by supplying a sample and an eluting solution to a column holding a column package, being provided with a means for making a ratio between oxyhemoglobin and deoxyhemoglobin in the column constant per measurement.

EXPLANATION OF REFERENCES

Figure 1:
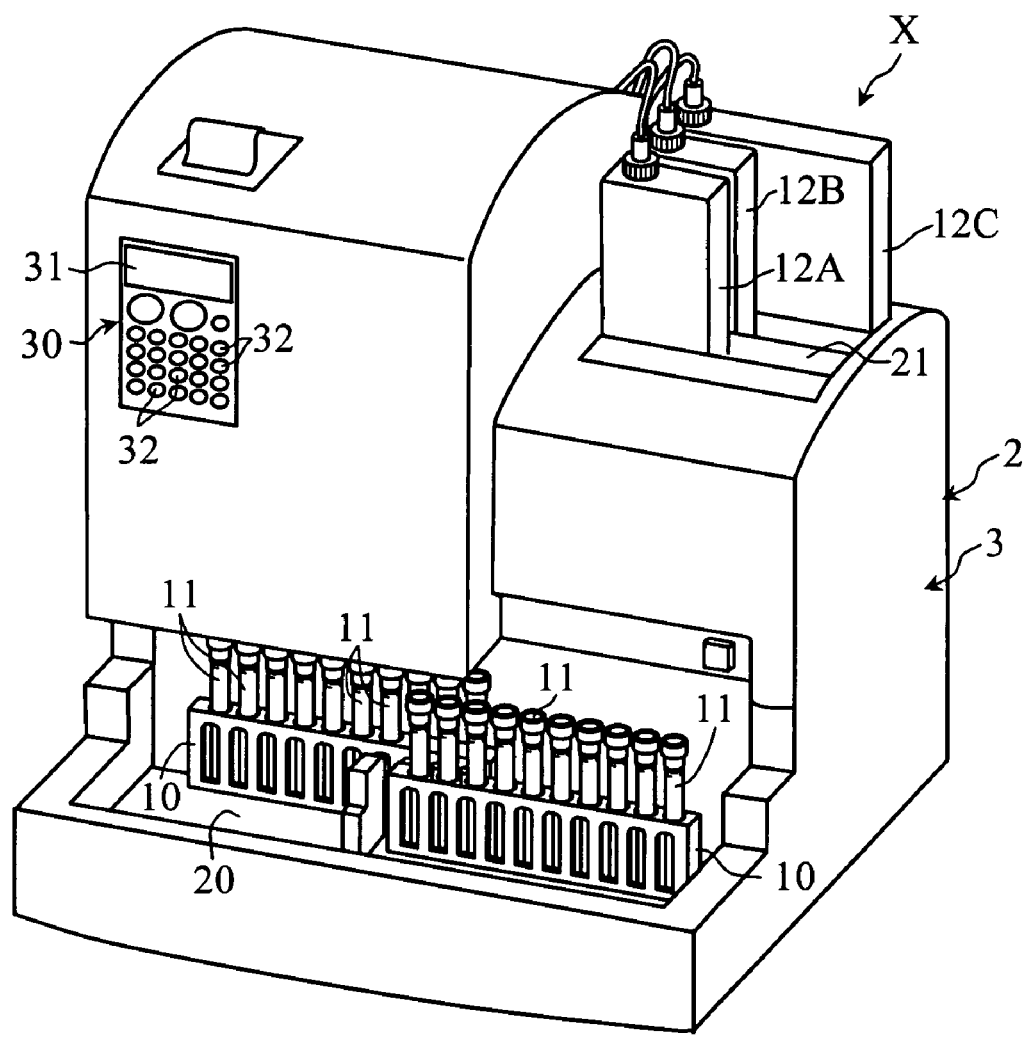
FIG. 1 is an entire perspective diagram showing an example of an HPLC apparatus according to the present invention.

X: HPLC apparatus
12A, 12B, 12C: eluting solution bottle
13: blood sample
13A: blood plasma layer
13B: blood cell layer
13C: interface
4: deaeration unit (deaerator)
40, 40A, 40B, 40C: temperature measurement part
41A, 41B, 41C: decompression space
42A, 42B, 42C: spiral tube
43: pump
5: sample adjustment unit
50: interface detection mechanism
51: nozzle
54: bubbling mechanism
6: analysis unit
60: analysis column
61: manifold
7: photometric unit (detection mechanism)
80A, 80B, 80C: pipe
81A, 81B, 81C: pipe
84: pipe
86: pipe

BEST MODE FOR CARRYING OUT THE INVENTION

Hereinafter, the specific examples of the present invention will be described with reference to FIGS. 1 to 7.

Figure 2:
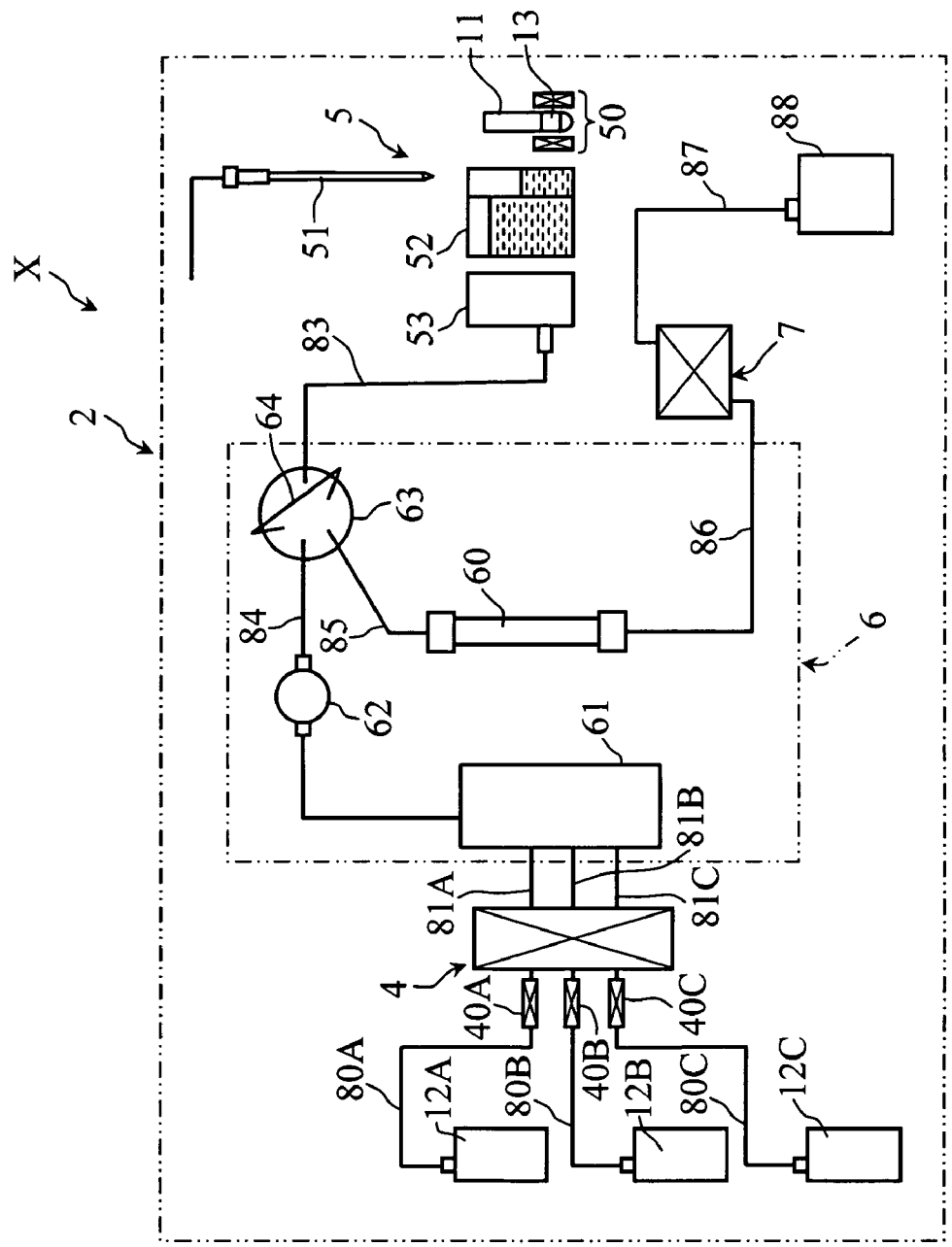
FIG. 2 is a schematic block diagram of the HPLC apparatus shown in FIG. 1.

An HPLC apparatus X shown in FIGS. 1 and 2 is configured in such a manner that, setting a blood collection tube 11 that is held by a rack 10 on a table 20, a density of glycohemoglobin in whole blood is automatically measured. This HPLC apparatus X is provided with a plurality of eluting solution bottles 12A, 12B, and 12C (three in the drawing) and a main body of the apparatus 2.

Respective eluting solution bottles 12A, 12B, and 12C hold an eluting solution to be supplied to an analysis column 60 to be described later and they are arranged in a holder part 21 in the main body of the apparatus 2. As the eluting solution, buffers having different pH and salt concentrations are used, for example.

The main body of the apparatus 2 has a deaeration unit 4, a sample adjustment unit 5, an analysis unit 6, and a photometric unit 7, which are contained in the inside of a package 3, in addition to the above-described table 20 and holder part 21.

The table 20 is configured so as to move a blood collection tube 11, which is held by the rack 10, to a position where blood of the blood collection tube 11 can be collected by means of a nozzle 51 in the sample adjustment unit 5 to be described later, by moving the rack 10 which is set on a predetermined region.

In the package 3, an operational panel 30 and a display panel 31 are provided. The operational panel 30 is provided with a plurality of operational buttons 32. By operating the operational buttons 32, it is possible to generate a signal for carrying out various operations (the analysis operation and the print operation or the like) or to make various settings (setting of an analysis condition and an ID input of an examinee or the like). The display panel 31 serves to display an analysis result and an error as well as to display an operational procedure upon setting and an operational state or the like.

Figure 3:
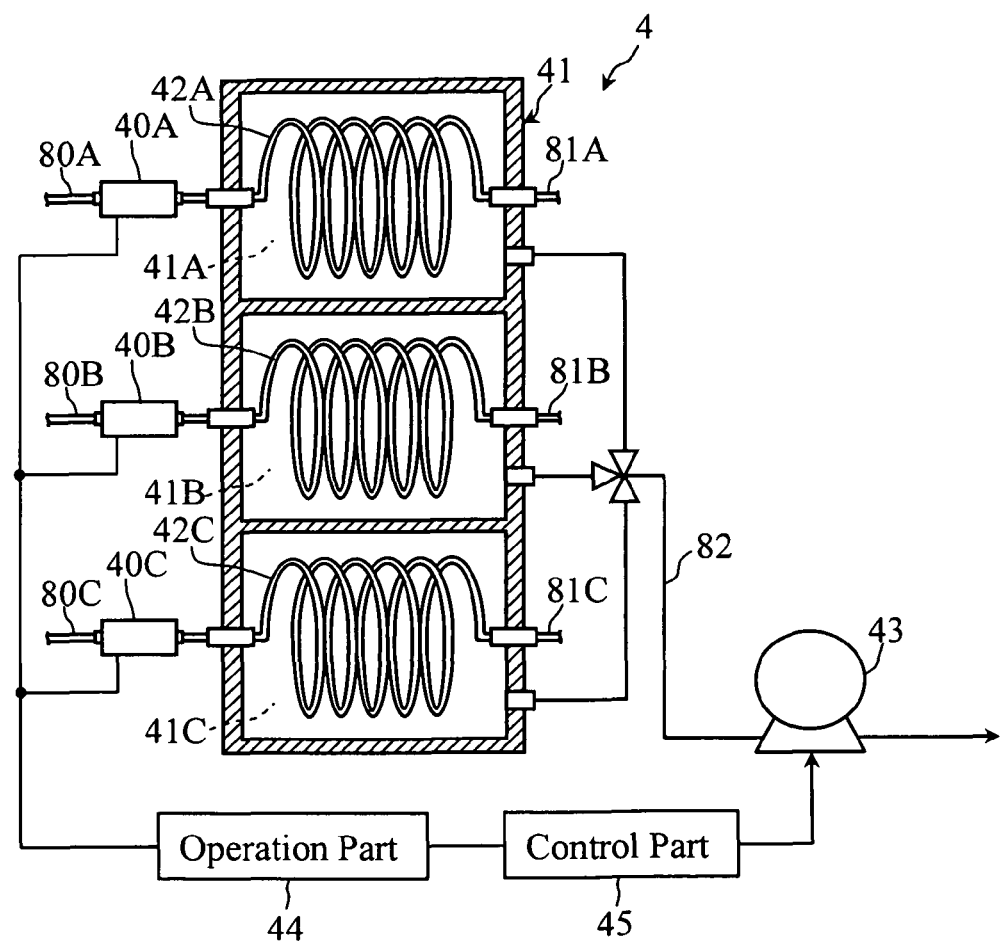
FIG. 3 is a piping diagram showing a part for explaining a deaeration unit in the HPLC apparatus shown in FIG. 1 in section.

As shown in FIG. 2, the deaeration unit 4 serves to remove the dissolved gas from the eluting solution before supplying the eluting solution to the analysis unit 6 (an analysis column 60), and is connected to the eluting solution bottles 12A, 12B, and 12C via pipes 80A, 80B, and 80C and to a manifold 61 of the analysis unit 6 via pipes 81A, 81B, and 81C. As shown in FIG. 3, the deaeration unit 4 has temperature measurement parts 40A, 40B, and 40C, a chamber 41, a plurality of spiral tubes 42A, 42B, and 42C (three in the drawing), a pump 43, an operation part 44, and a control part 45.

The temperature measurement parts 40A, 40B, and 40C serve to measure the temperature of the eluting solution to be introduced into the chamber 41, and they are mounted in the vicinity of the chamber 41 in the pipes 80A, 80B, and 80C. These temperature measurement parts 40A, 40B, and 40C are provided with a thermistor (illustration omitted), which is arranged in the inside of pipes 80A, 80B, and 80C, and are configured so as to be capable of directly measuring the temperature of the eluting solution filled in the pipes 80A, 80B, and 80C. The measurement results in these temperature measurement parts 40A, 40B, and 40C are outputted to the operation part 44.

The chamber 41 serves to define a plurality of decompression spaces 41A, 41B, and 41C (three in the drawing) and to contain the spiral tubes 42A, 42B, and 42C.

The spiral tubes 42A, 42B, and 42C serve to distribute the eluting solution in the inside thereof and to permeate the dissolved gas in the eluting solution, and they are formed as a hollow by a publicly-known gas permeable film such as silicon. These spiral tubes 42A, 42B, and 42C are formed in a spiral shape to secure the lengths of flow channels within the decompression spaces 41A, 41B, and 41C to be long, and they are configured so as to be capable of securing a detention time of the eluting solution in the decompression spaces 41A, 41B, and 41C to be long, while securing contact areas with gas in the decompression spaces 41A, 41B, and 41C to be large.

A pump 43 serves to decompress decompression spaces 41A, 41B, and 41C by emitting the gas in the decompression spaces 41A, 41B, and 41C via a pipe 82. This pump 43 is operationally controlled by a control part 45.

The operation part 44 serves to calculate a control amount for the pump 43 on the basis of the temperature data of the eluting solution to be transmitted from the temperature measurement parts 40A, 40B, and 40C. This operation part 44 is configured so as to calculate the control amount for the pump 43 according to a relational expression between the temperature of the eluting solution, which is determined in advance, and an absorption pressure of the pump 43, for example. The absorption pressure is adjusted by the open state of a valve in the pump 43 (illustration omitted) or a driving power (a driving voltage) of the pump 43, for example.

The control part 45 serves to control the operation of the pump 43 in accordance with the control amount that is calculated by the operation part 44.

The operation part 44 and the control part 45 are configured by CPU, ROM, and RAM, for example.

As shown in FIG. 2, the sample adjustment unit 5 serves to adjust the sample to be introduced from a component of a blood cell collected from the blood collection tube 11 into an analysis column 60. This sample adjustment unit 5 has an interface detection mechanism 50, a nozzle 51, an adjustment solution tank 52, and a diluting tank 53.

Figure 4:
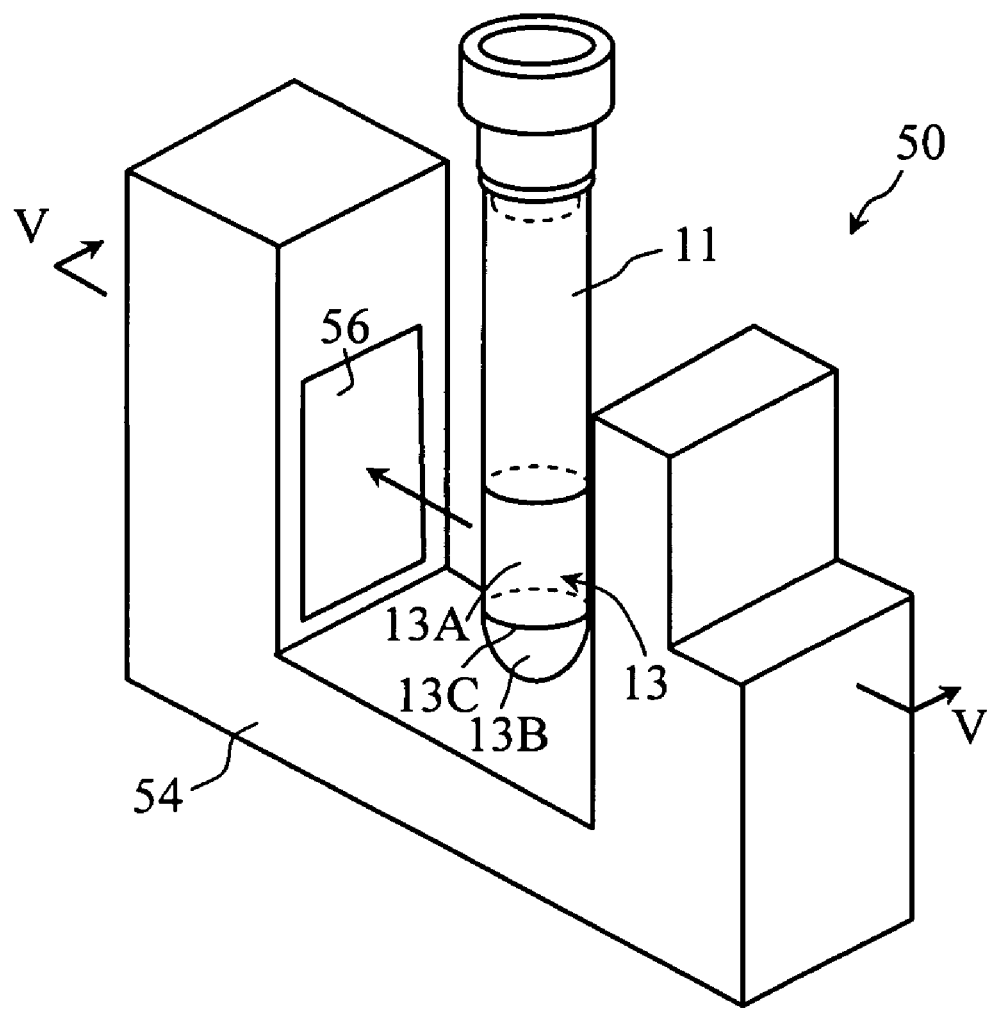
FIG. 4 is a perspective view for explaining an interface detection mechanism of the HPLC apparatus shown in FIG. 1.
Figure 5:
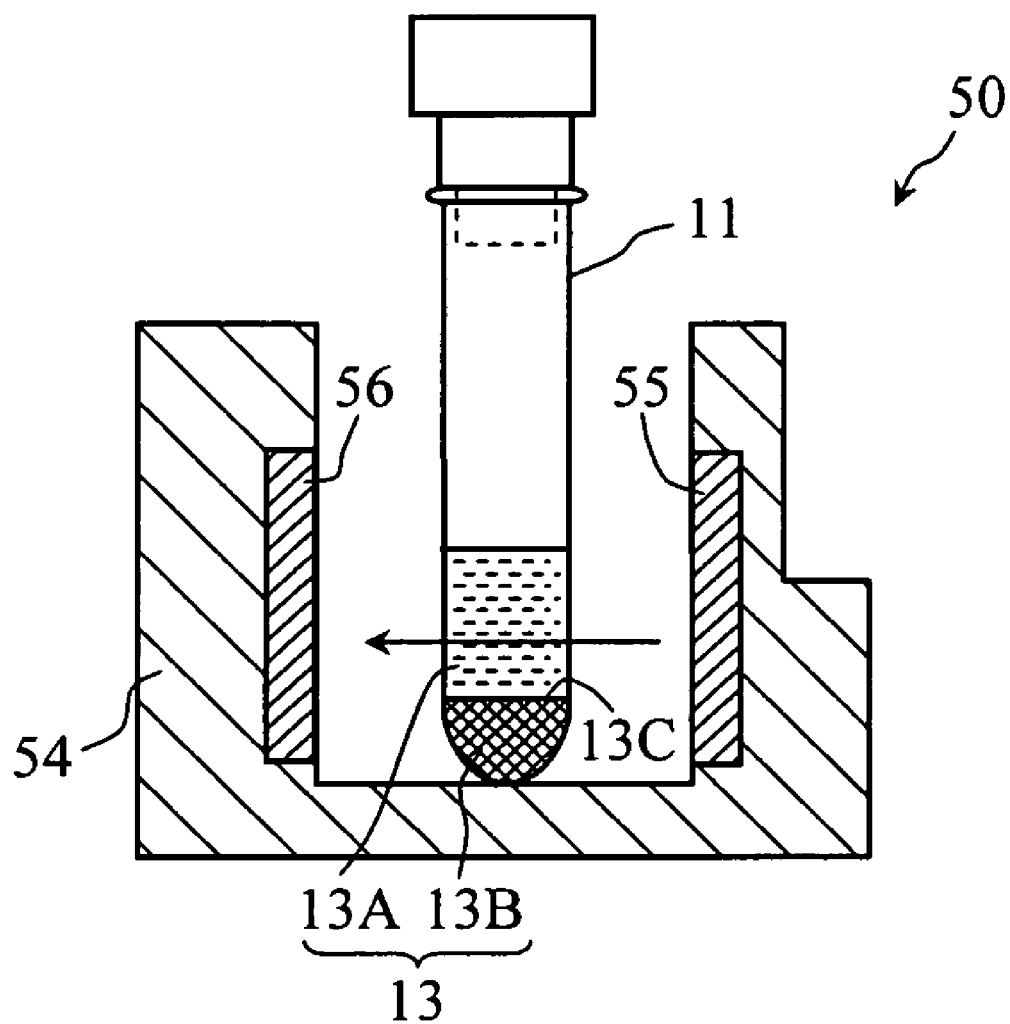
FIG. 5 is a sectional view along a V-V line in FIG. 4.
Figure 6:
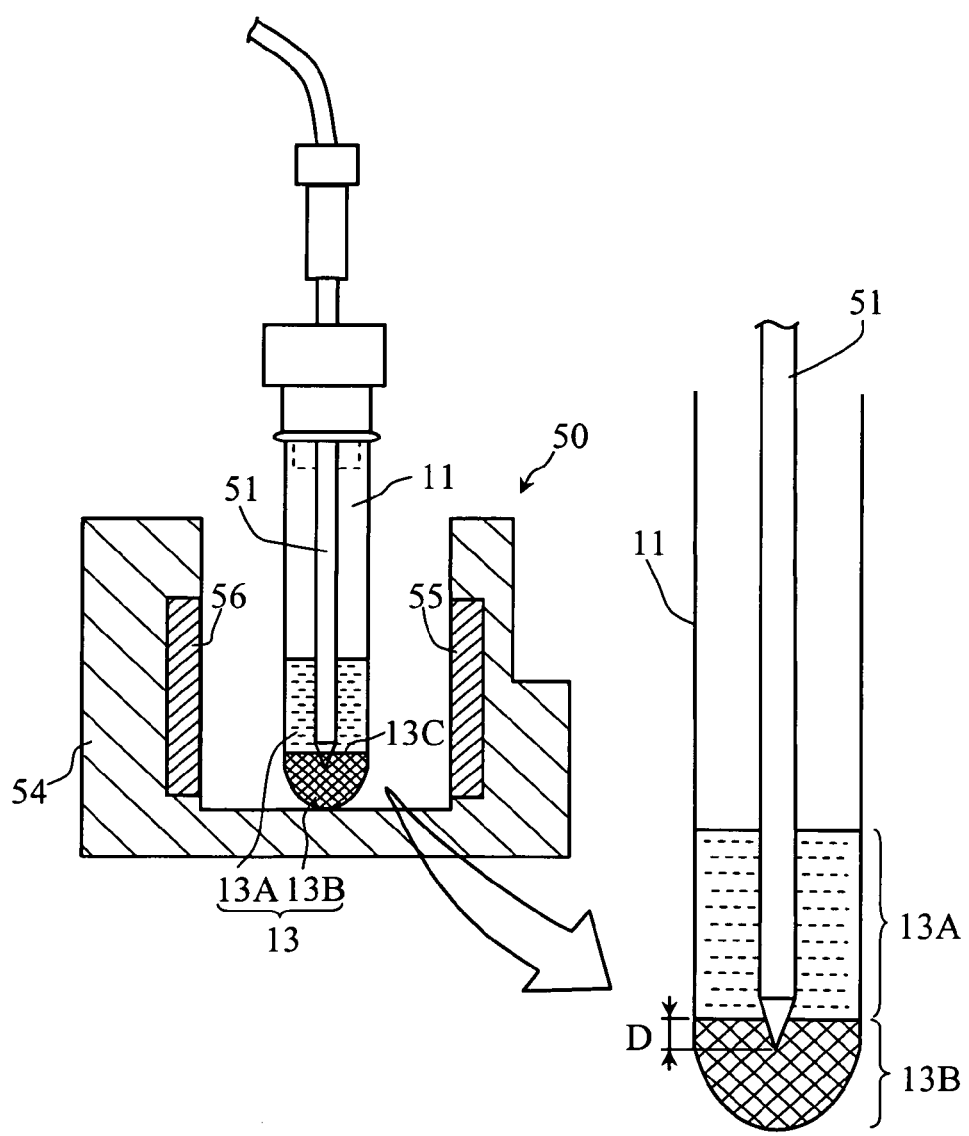
FIG. 6 is a sectional view and a substantial part enlarged view for explaining a sample collecting method.

As shown in FIGS. 4 to 6, the interface detection mechanism 50 serves to detect an interface 13C between a blood plasma layer 13A and a blood cell layer 13B of a blood sample 13 of the blood collection tube 11 by an optical method, and it is configured as a photo sensor of a transmission type. This interface detection mechanism 50 has a light irradiating part 55 and a light receiving part 56, which are arranged facing each other to a U-shaped holder 54. The blood collection tube 11 is moved so as to cut across a space between the light irradiating part 55 and the light receiving part 56 as being held by the rack 10.

The light irradiating part 55 can irradiate a light within a predetermined range in a vertical direction in the blood collection tube 11, and a liner light source capable of irradiating a light, of which peak wavelength is within a wavelength range (500 to 570 nm) having a large light absorption in a red blood cell, is used, for example. As the light irradiating part 55, for example, one configured so as to be capable of scanning a dotted-like light source in a vertical direction can be also adopted. On the other hand, the light receiving part 56 serves to receive a light that transmits the blood collection tube 11, and it can receive a light within a predetermined range in a vertical direction in the blood collection tube 11. As such a light receiving part 56, for example, a line sensor or an area sensor can be used.

It is obvious that the interface detection mechanism 50 may have a photo sensor of a reflection type for detecting the light that is reflected on the surface of the blood collection tube 11, for example, and it may be configured so as to detect the interface 13C between the blood plasma layer 13A and the blood cell layer 13B, for example, by change of an insertion resistance when the nozzle 51 is introduced into the blood collection tube 11, or by change of an electric resistance, other than the optical method.

As shown in FIG. 2 and FIG. 6, the nozzle 51 serves to collect various liquids including the blood sample 13 of the blood collection tube 11. The nozzle 51 can absorb and discharge the liquid and can be moved in a vertical direction and a horizontal direction. The operation of this nozzle 51 is controlled by a control means (not illustrated), and in the case of collecting the blood sample 13 from the blood collection tube 11, on the basis of the interface 13C that is detected by the interface detection mechanism 50, the nozzle is operated so as to collect the blood cell component from the blood cell layer 13B slightly below the interface 13C.

The adjustment solution tank 52 shown in FIG. 2 holds an adjustment solution for adjusting the sample for introduction to be introduced into the analysis column 60 on the basis of the blood sample 13. In this adjustment solution tank 52, as an adjustment solution, a hemolytic solution for hemolyzing a red blood cell and a dilute solution for diluting the hemolytic solution or the like are held. As a dilute solution, it is preferable that one having a high degree of oxygen saturation, for example, one having a degree of oxygen saturation of 85% or more is used. For collecting the adjustment solution from the adjustment solution tank 52, the nozzle 51 is used.

The diluting tank 53 serves to hemolyze the red blood cell in the blood sample 13, provides a field for adjusting the sample for introduction by diluting the hemolytic solution, and intense a degree of oxygen saturation (a density of a dissolved oxygen) in the sample for introduction by bringing the sample for introduction into contact with air. This diluting tank 53 is connected to an injection valve 63 in the analysis unit 6 to be described later via a pipe 83, and the diluting tank 53 is configured so as to be capable of introducing the sample for introduction, which is adjusted in the diluting tank 53, into the analysis column 60 via the injection valve 63. In addition, the diluting tank 53 has an upper part, which is opened in order to bring the sample for introduction into contact with air.

As shown in FIG. 2, the analysis unit 6 serves to control absorption and desorption of a biogenic substance for a column packing of the analysis column 60, and provide various biogenic substances to the photometric unit 7, and the temperature of the analysis unit 6 is controlled by a temperature adjusting mechanism (not illustrated). A preset temperature in the analysis unit 6 is determined to be about 40° C., for example. The analysis column 60 holds the column package for selectively absorbing the hemoglobin in the sample. As a column package, for example, a methacrylate ester copolymer is utilized.

The analysis unit 6 has a manifold 61, a solution sending pump 62, and an injection valve 63 in addition to the analysis column 60.

The manifold 61 serves to selectively supply the eluting solution to the injection valve 63 from specific eluting solution bottles 12A, 12B, and 12C among a plurality of the eluting solution bottles 12A, 12B, and 12C. This manifold 61 is connected to the decompression spaces 41A, 41B, and 41C of the deaeration unit 4 (the spiral tubes 42A, 42B, and 42C) via the pipes 81A, 813, and 81C, and is connected to the injection valve 63 via a pipe 84.

Here, as the pipes 81A, 81B, and 81C, one formed by a material, of which oxygen permeability is entirely low, for example, nylon, polyether ether ketone (PEEK), polyethylene or stainless-steel (SUS) is used.

The solution sending pump 62 serves to give a power for moving the eluting solution to the injection valve 63, and is mounted in the middle of the pipe 84. The solution sending pump 62 is operated so that a feed rate of the eluting solution is in the range of 1.0 to 2.0 ml/min.

The injection valve 63 collects a predetermined amount of the sample for introduction and enables to introduce the sample for introduction into the analysis column 60, and is provided with a plurality of introduction ports and discharge ports (illustrations omitted). An injection loop 64 is connected to this injection valve 63. This injection loop 64 can hold a predetermined amount (for example, several μL) of liquid, and by accordingly switching the injection valve 63, it is possible to select the state such that the injection loop 64 is communicated with the diluting tank 53 and the sample for introduction is supplied from the diluting tank 53 to the injection loop 64, the state such that the injection loop 64 is communicated with the analysis column 60 via the pipe 85 and the sample for introduction is introduced from the injection loop 64 to the analysis column 60, or the state such that a cleaning fluid is supplied from a cleaning tank (not illustrated) to the injection loop 64. As such an injection valve 63, for example, a hexagonal valve can be used.

Figure 7:
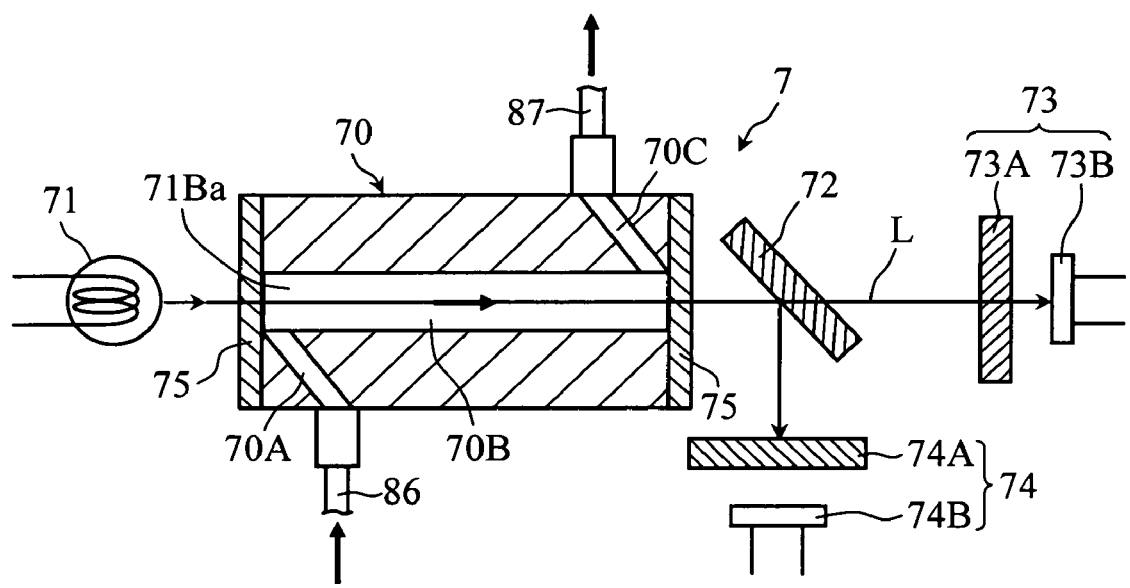
FIG. 7 is a sectional view for explaining a photometric unit in the HPLC apparatus shown in FIG. 1.

As shown in FIG. 7, the photometric unit 7 can optically detect hemoglobin contained in a desorption solution from the analysis column 60, and has a photometric cell 70, a light source 71, a beam splitter 72, a light receiving system for measurement 73, and a light receiving system for reference 74.

The photometric cell 70 serves to define the photometric area. This photometric cell 70 has an introduction flow channel 70A, a photometric flow channel 70B, and a discharge flow channel 70C, and these flow channels 70A, 70B, and 70C are communicated with each other in sequence. The introduction flow channel 70A serves to introduce the separated liquid from the analysis column 60 (refer to FIG. 2) into the photometric flow channel 70B to be connected to the analysis column 60 via the pipe 86. As the pipe 86, one formed by a material, of which oxygen permeability is entirely low, for example, nylon, polyether ether ketone (PEEK), polyethylene or stainless-steel (SUS) is used as well as the pipes 81A, 81B, and 81C, which have been previously described. The photometric flow channel 70B allows the separated liquid, which is an object of photometry, to be distributed, and provides a field where the separated liquid is photometrically measured, and is linearly formed. This photometric flow channel 70B has the opened opposite ends with the opposite end portions being covered with a transparent cover 75. The discharge flow channel 70C serves to discharge the separated liquid of the photometric flow channel 70B, and is connected to a waste fluid tank 88 via the pipe 87 (refer to FIG. 2).

A light source 71 serves to irradiate the light to the separated liquid, which is distributed through the photometric flow channel 70B. This light source 71 is arranged facing to an end face 70Ba (the transparent cover 75) of the photometric flow channel 70B so that an optical shaft L passes through a center of the photometric flow channel 70B. As the light source 71, one that can emit a light in the range of a wavelength including a wavelength 415 nm, which is the longest absorption wavelength of oxyhemoglobin, and a reference wavelength 500 nm, for example, a halogen lamp is utilized. It is obvious that, as the light source 71, one other than the halogen lamp, for example, one, which is provided with 1 or plural LED devices, can be also used.

A beam splitter 72 serves to divide the light that transmits through the photometric flow channel 70B among the lights emitted from the light source 71 and allow the divided lights to enter the light receiving system for measurement 73 and the light receiving system for reference 74, and on the optical shaft L, the beam splitter 72 is arranged being inclined at 45 degrees. As the beam splitter 72, various publicly-known devices such as a half mirror can be used.

The light receiving system for measurement 73 serves to selectively receive the light of 415 nm, which is the longest absorption wavelength of oxyhemoglobin, and is arranged on the optical shaft L. This light receiving system for measurement 73 is provided with an interference filter 73A for selectively transmitting the light of 415 nm and a light receiving device 73B for receiving the light transmitted through the interference filter 73A. As the light receiving device 73B, a photo diode can be used.

The light receiving system for reference 74 selectively receives the light of 500 nm, which is a reference wavelength, among the lights, of which light paths are changed being reflected in the beam splitter 72. This light receiving system for reference 74 is provided with an interference filter 74A for selectively transmitting the light of 500 nm and a light receiving device 74B for receiving the light transmitted through the interference filter 74A. As the light receiving device 74B, a photo diode can be used.

Next, the operation of the HPLC apparatus X will be described.

In the case of measuring glycohemoglobin by using the HPLC apparatus X, at first, the rack 10 is set at a predetermined region of the table 20 with the blood collection tube 11, in which the blood sample 13 is filled, being held by the rack 10. The blood sample 13 of the blood collection tube 11 has been separated into the blood plasma layer 13A and the blood cell layer 13B in advance. Such separation can be made by using a centrifugal machine or spontaneously precipitating a blood cell component.

The separation of the blood plasma layer 13A and the blood cell layer 13B may be made in the HPLC apparatus X incorporating the centrifugal machine in the HPLC apparatus X, or, it may be made by leaving the blood sample 13 at rest for a predetermined time with the blood collection tube 11 being set on the table 20.

In the case that the instruction to start the measurement is confirmed, the HPLC apparatus X moves the rack 10 on the table 20, and it collects the blood sample 13 from the blood collection tube 11 in target. The instruction to start the measurement is effected when a user operates a predetermined operational button 32 of the HPLC apparatus X.

The blood sample 13 is collected from the blood collection tube 11 in an area that is separated downward from the interface 13C by a predetermined distance D after detecting the interface 13C between the blood plasma layer 13A and the blood cell layer 13B in the interface detection mechanism 50. More specifically, in the interface detection mechanism 50, irradiating the light from the light irradiating part 55 to the blood collection tube 11, the light transmitted through the blood collection tube 11 is received by the light receiving part 56. Here, in the case the light irradiating part 55 irradiates the light, of which peak wavelength is within the wave length range having a large light absorption in a red blood cell, comparing to the blood plasma layer 13A, the light absorption in the blood cell layer 13B becomes larger. Therefore, in the interface detection mechanism 50, by detecting the part where the light absorption is remarkably changed on the basis of the light receiving amount in the light receiving part 56, it is possible to detect the interface 13C between the blood plasma layer 13A and the blood cell layer 13B.

In the interface detection mechanism 50, in the case that detection of the interface 13C is terminated, by operating the nozzle 51 on the basis of the detection result in the interface detection mechanism 50, the blood sample 13 is collected from the upper layer of the blood cell layer 13B. In this case, the nozzle 51 has a front end, which is placed in an area where a distance D from the interface 13C between the blood plasma layer 13A and the blood cell layer 13B is in the range of 5 to 30% to the thickness of the blood cell layer 13B, for example, or an area where the distance D is in the range of 0.5 to 5.0 mm, and the nozzle 51 is operated so as to collect the blood sample 13 from the blood collection tube 11 by carrying out the absorption operation in this state.

Here, in the case that the blood cell component is separated toward the bottom part of the blood collection tube 11 by centrifugal separation or the like, the degree of oxygen saturation (the dissolved oxygen density) of the upper layer part of the blood cell layer 13B is higher than the lower layer part, and in the case that the blood sample 13 has been left at rest, the degree of oxygen saturation (the dissolved oxygen density) of the upper layer part of the blood cell layer 13B where a distance from an air layer is short, is higher than the lower layer part. Therefore, by controlling the operation of the nozzle 51 on the basis of the detection result of the interface 13C in the interface detection mechanism 50 and collecting the blood sample 13 from the upper layer part of the blood cell layer 13B, it is possible to collect the blood sample 13 having a high degree of oxygen saturation (the dissolved oxygen density). In addition, in the case of collecting the blood sample 13 from the part where the distance D from the interface 13C is located in a further area, it is possible to reliably collect the blood sample 13 from the upper layer part of the blood cell layer 13B.

The blood sample 13 that is collected by the nozzle 51 is supplied to the diluting tank 53 by operating the nozzle 51. Further, a hemolytic agent and a dilute solution are supplied from the adjustment solution tank 52 to the diluting tank 53 in sequence, and by mixing a liquid in the diluting tank 53 by pipetting using the nozzle 51, the sample for introduction is adjusted.

The sample for introduction that is adjusted in the diluting tank 53 is supplied to the injection loop 64 after being brought into contact with air for a predetermined time in the diluting tank 53, and held in the injection loop 64.

In the case of bringing the sample for introduction into contact with air for a predetermined time, the dissolved oxygen density of the sample for introduction is increased. Thus, in the case that the degree of oxygen saturation of the sample for introduction is increased, it is possible to supply the sample for introduction having a high dissolved oxygen density to the injection loop 64, further, to the analysis column 60. In other words, in hemoglobin contained in the sample for introduction, a ratio of oxy hemoglobin can be made large.

Here, a contact time of the sample for introduction and air (an air opening time) is defined to be 1 to 2 minutes, for example. This is because, when the air opening time is too short, a sufficient amount of oxygen cannot be dissolved for the sample for introduction, and on the other hand, when the air opening time is too long, a time after adjusting the sample for introduction till introduction of the sample for introduction into the injection loop 64 becomes long and thereby, a measurement time becomes long.

In addition, in the case of using the solution having a high degree of oxygen saturation as a dilute solution, for example, using the solution, of which degree of oxygen saturation is 85% or more, it is not always necessary to open the diluted sample for introduction to air. In other words, in the case of using the dilute solution having a high degree of oxygen saturation, even when using the closed diluting tank 53, by leaving the diluting tank 53 for a predetermined time (for example, one minute or more), the degree of oxygen saturation of the diluted sample for introduction can be heightened, and a ratio of oxyhemoglobin can be made large.

Further, in the HPLC apparatus X, in the case that the instruction to start the measurement is confirmed, the eluting solution is supplied to the injection valve 63. The eluting solution is supplied from the eluting solution bottles 12A, 12B, and 12C to the injection valve 63 via the deaeration unit 4 and the manifold 61 by a power of the solution sending pump 62. In addition, from which eluting solution bottles 12A, 12B, and 12C among a plurality of eluting solution bottles 12A, 12B, and 12C the eluting solutions are supplied is selected by controlling the manifold 61.

In the deaeration unit 4, the temperature of the eluting solution is measured in the temperature measurement parts 40A, 40B, and 40C during distribution of the eluting solution through the pipes 80A, 80B, and 80C. The measurement results by these temperature measurement parts 40A, 40B, and 40C are outputted to the operation part 44, and in the operation part 44, the control amount of the pump 43 is calculated on the basis of the temperature data of the eluting solution to be transmitted from the temperature measurement parts 40A, 403, and 40C. This operation part 44 calculates the control amount for the pump 43 according to a relational expression between the temperature of the eluting solution, which is determined in advance, and an absorption pressure of the pump 43 (for example, an open state of a valve in the pump 43 (illustration omitted) or a driving power (a driving voltage) of the pump 43), for example. In the case that a control amount of the pump 43 is calculated in the operation part 44, the control part 45 controls operation of the pump 43 in accordance with the control amount calculated by the operation part 44. Thereby, the amount of the gas to be discharged from the decompression spaces 41A, 41B, and 41C via the pipe 82 is adjusted depending on the temperature of the eluting solution (the density of the dissolved oxygen), and as a result, in the deaeration unit 4, in accordance with the temperature of the eluting solution (the density of the dissolved oxygen), the degrees of decompression of the decompression spaces 41A, 41B, and 41C are adjusted by the pump 43.

On the other hand, the eluting solutions distributed through the pipes 80A, 803, and 80C are discharged from the spiral tubes 42A, 42B, and 42C after being distributed through the spiral tubes 42A, 42B, and 42C within the decompression spaces 41A, 41B, and 41C. In this case, the spiral tubes 42A, 42B, and 42C are formed by a material with a high gas permeability, and the decompression spaces 41A, 41B, and 41C are decompressed by the pump 43, so that, during distribution of the eluting solution through the spiral tubes 42A, 42B, and 42C, a dissolved gas including the dissolved oxygen is removed from the eluting solution. Then, in the deaeration unit 4, the degrees of decompression of the decompression spaces 41A, 41B, and 41C are adjusted according to the temperature of the eluting solution, so that, upon discharge of the eluting solution from the decompression spaces 41A, 41B, and 41C, regardless of the temperature of the eluting solution, the density of the dissolved oxygen in the eluting solution is made constant. Here, the temperature of the eluting solution is influenced by the temperature of the outside of the HPLC apparatus X (the environmental temperature), however, in the deaeration unit 4, it is possible to discharge the eluting solution, in which the density of the dissolved oxygen is made constant regardless of the environmental temperature. Thereby, even in the case that the environmental temperature is varied, or in the case that measurement is carried out under different environmental temperatures, it is possible to make the density of the dissolved oxygen in the eluting solution to be discharged from the deaeration unit 4 substantially constant.

The eluting solutions discharged from the decompression spaces 41A, 41B, and 41C (the spiral tubes 42A, 42B, and 42C) are supplied to the manifold 61 via the pipes 81A, 81B, and 81C, and thereafter introduced into the injection valve 63 via the pipe 84.

Here, as the pipes 81A, 81B, and 81C, one formed by a material having low oxygen permeability is used. Therefore, during distribution of the eluting solution to be supplied to the manifold 61 through the pipes 81A, 81B, and 81C, it is prevented that a gas such as oxygen from being absorbed in the eluting solution again. As a result, the eluting solution, of which degree of the dissolved oxygen is defined to be constant in the deaeration unit 4, will be supplied to the manifold 61 as accordingly maintaining that state.

The eluting solution supplied to the injection valve 63 is supplied to the analysis column 60 via the pipe 85. On the other hand, by carrying out the switching operation of the injection valve 63, the sample for introduction of the injection loop 64 is introduced into the analysis column 60 together with the eluting solution. In the case that a predetermined time has passed from start of introduction of the sample for introduction, by carrying out the switching operation of the injection valve 63, the eluting solution is continuously supplied to the analysis column 60 and the injection loop 64 is cleaned. On the other hand, at the same time as cleaning of the injection loop 64, adjusting the sample for introduction from the blood sample 13 of the blood collection tube 11 that is different from the above-described case in the same way as the above-described case, the sample for introduction is introduced into the injection loop 64 again after cleaning of the injection loop 64. Such adjustment, introduction, and cleaning of the sample for introduction are repeatedly carried out in accordance with the number of the blood collection tubes (the blood samples 13) that are the target of measurement while accordingly changing the injection valve 63.

On the other hand, in the analysis column 60, by introducing the sample for introduction therein, glycohemoglobin is absorbed to the column package. After allowing the column package to absorb glycohemoglobin, accordingly switching the kinds of the eluting solution to be supplied to the analysis column 60 by the manifold 61, glycohemoglobin that is absorbed to the column package is desorbed.

In this case, even when supplying a plurality of solutions, of which feed rates are mutually different, to the analysis column 60, and that a time passing through the pipes 81A, 81B, and 81C (a detention time) is different for each eluting solution among the plural kinds of the eluting solutions, re-absorption of oxygen in the pipes 81A, 81B, and 81C is accordingly prevented. Therefore, even if the kinds of the eluting solution (the feeding rate) is changed upon measurement of one blood sample 13 in the analysis column 60, it is accordingly prevented that the amount of the dissolved oxygen in the eluting solution moving in the analysis column 60 from being changed. As a result, because of re-absorption of oxygen in the pipes 81A, 81B, and 81C, preventing the measurement result from being deviated from a true value, an accurate measurement can be made.

In addition, it is assumed that a difference due to a manufacturing process is generated with respect to the oxygen permeability of the pipes 81A, 81B, and 81C mutually in a plurality of the HPLC apparatuses X, and in this case, the re-absorption amounts in the pipes 81A, 81B, and 81C mutually in a plurality of the HPLC apparatuses X are different. Therefore, it is feared that a difference is generated in the degree of accuracy, mutually in a plurality of the HPLC apparatuses X, however, by using the pipes 81A, 81B, and 81C having low oxygen permeability, it is possible to prevent the influence by a difference due to a manufacturing process of the pipes 81A, 81B, and 81C as much as possible.

The desorption solution containing glycohemoglobin to be discharged from the analysis column 60 is supplied to the photometric cell 70 of the photometric unit 7 via the pipe 86. The desorption solution is introduced into the photometric cell 70 via the pipe 86 and the introduction flow channel 70A, and this desorption solution is introduced to the waste fluid tank 88 via the pipe 87 after passing through the photometric flow channel 70B and the discharge flow channel 70C.

Here, as the pipe 86, one formed by a material having low oxygen permeability is used. Therefore, during supply of the separated liquid from the analysis column 60 to the photometric unit 7 (the photometric cell 70) via the pipe 86, it is prevented that gas such as oxygen is absorbed again in the separated liquid. As a result, the separated liquid is supplied from the analysis column 60 to the photometric unit 7 as the density of the dissolved oxygen is maintained constant. In addition, as same as the case of the pipes 81A, 81B, and 81C, it is possible to prevent a decrease in accuracy in measurement because of a difference due to a manufacturing process for oxygen permeability of the pipe 86 mutually in a plurality of the HPLC apparatuses X.

In the photometric unit 7, when the separated liquid passes through the photometric flow channel 70B, a light is continuously irradiated to the separated liquid by the light source 71. On the other hand, the light transmitted through the photometric flow channel 70B is divided in the beam splitter 72, and then, this light is received by the light receiving system for measurement 73 and the light receiving system for reference 74. In the light receiving system for measurement 73, the light of 415 nm, which is the longest absorption wavelength of oxyhemoglobin transmitted through the interference filter 73A, is selectively received by the light receiving device 73B. On the other hand, in the light receiving system for reference 74, the light of 500 nm, which is the reference wavelength transmitted through the interference filter 74A, is selectively received by the light receiving device 74B.

Results of light reception in the light receiving devices 73A and 74A are outputted to the operation circuit (not illustrated), and in this operation circuit, a chromatogram of hemoglobin and a density of glycohemoglobin (the ratio of glycohemoglobin in the total amount of hemoglobin) is calculated. The calculation result of the operation circuit is displayed on the display panel 31, and automatically or by the button operation by the user, this calculation result is printed.

In such an HPLC apparatus X, the density of the dissolved oxygen in the eluting solution is made constant in the deaeration unit 4, and the eluting solution from the deaeration unit 4 is supplied to the manifold 61 by the pipes 81A, 81B, and 81C having a low oxygen permeability as maintaining the density of the dissolved oxygen in the eluting solution substantially constant. On the other hand, the manifold 61 forms the analysis unit 6 together with the injection valve 63 and the analysis column 60, and the temperature of the analysis unit 6 is adjusted to be kept constant. Therefore, in the eluting solution to be supplied from the manifold 61 to the analysis column 60, change of the density of the dissolved oxygen because of change of a temperature is hardly produced. As a result, it is possible to supply the eluting solution, of which density of the dissolved oxygen is made constant, to the analysis column 60 regardless of variation of an environmental temperature. Accordingly, the HPLC apparatus X is capable of preventing instability of a measurement result, which is caused by variation of the density of the dissolved oxygen in the eluting solution or the like.

On the other hand, the density of the dissolved oxygen in the sample for introduction to be introduced into the analysis column 60 is adjusted on the basis of the blood sample 13 that is collected from the upper part of the blood cell layer 13B, and after adjusting the density of the dissolved oxygen, the sample for introduction is substantially saturated in the diluting tank 53 before being introduced into the analysis column 60. Therefore, the density of the dissolved oxygen is standardized, so that the sample for introduction to be introduced into the analysis column 60 can be supplied to the analysis column 60 with a ratio between oxyhemoglobin and deoxyhemoglobin in the sample for introduction being made constant. Further, re-absorption of oxygen at the pipe 86 is prevented during supply of the separated liquid from the analysis column 60 to the photometric unit 7. As a result, for the photometric unit 7, a variation in a ratio between oxyhemoglobin and deoxyhemoglobin per sample for introduction is prevented, and thereby, it is possible to prevent a variation of a measurement result, which is caused by this variation.

Figure 8A:
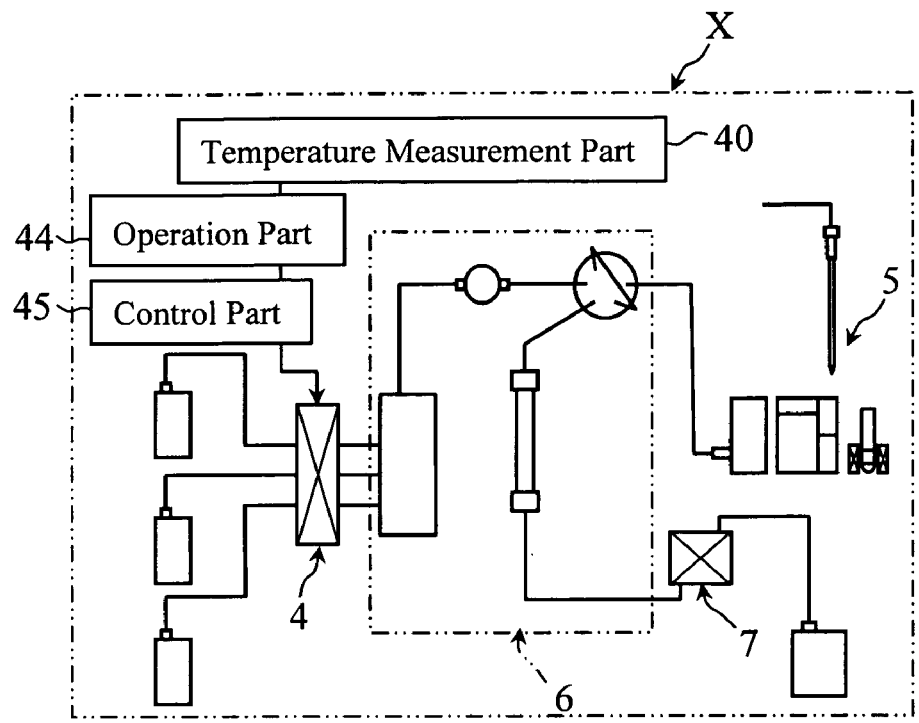
FIG. 8 is a schematic block diagram for explaining other example of the HPLC apparatus according to the present invention, which is equivalent to FIG. 2.
Figure 8B:
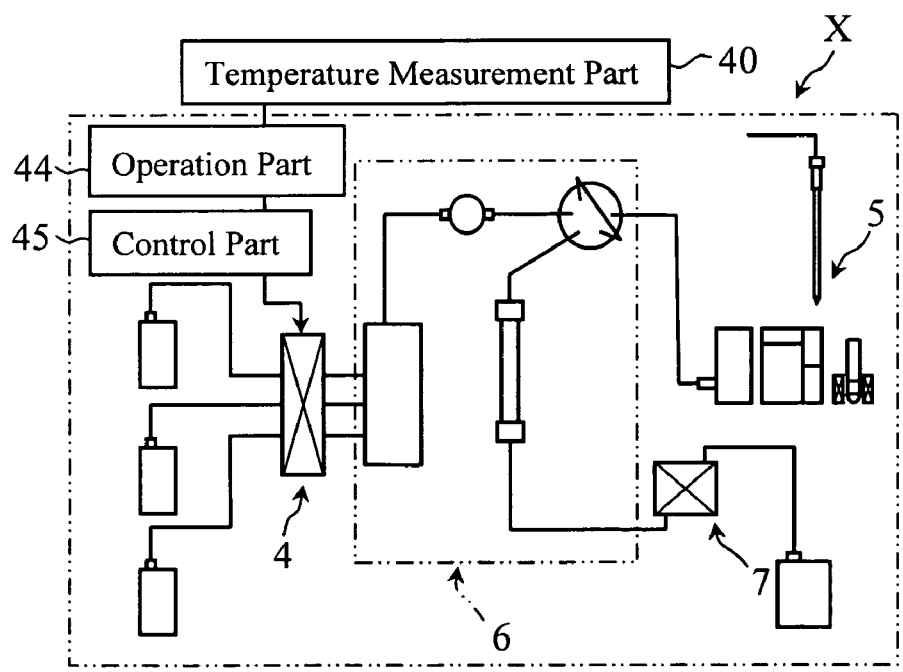

The present invention is not limited to the above-described embodiment and can be variously modified. For example, upon adjustment of the degree of decompression of the decompression spaces 41A, 41B, and 41C of the deaeration unit 4, it is not always necessary to directly measure the temperature of the eluting solution by providing the temperature measurement parts 40A, 40B, and 40C to the pipes 80A, 80B, and 80C. For example, the present invention may be configured in such a manner that, as shown in FIG. 8A, by mounting the temperature measurement part 40 in the inside of the apparatus, the temperature of the inside of the apparatus is measured, and as shown in FIG. 8B, by mounting the temperature measurement part 40 outside of the apparatus, the environmental temperature of the outside of the apparatus (for example, a peripheral temperature of the apparatus X, a temperature of an exterior wall of the package 3 of the apparatus X, or temperatures of the eluting solution bottles 12A, 12B, and 12C) is measured. In addition, the temperature measurement part may be mounted in the pipes 81A, 81B, and 81C that are connected to the manifold 61 in the deaeration unit 4, the spiral tubes 42A, 42B, and 42C, and the decompression spaces 41A, 41B, and 41C (refer to FIG. 3). Further, in place of the temperature measurement parts 40A, 40B, and 40C shown in FIG. 2 and FIG. 3, a dissolved oxygen measuring sensor (an oxygen sensor) may be provided to the pipes 80A, 80B, and 80C, the pipes 81A, 81B, and 81C, or the spiral tubes 42A, 42B, and 42C.

Figure 9:
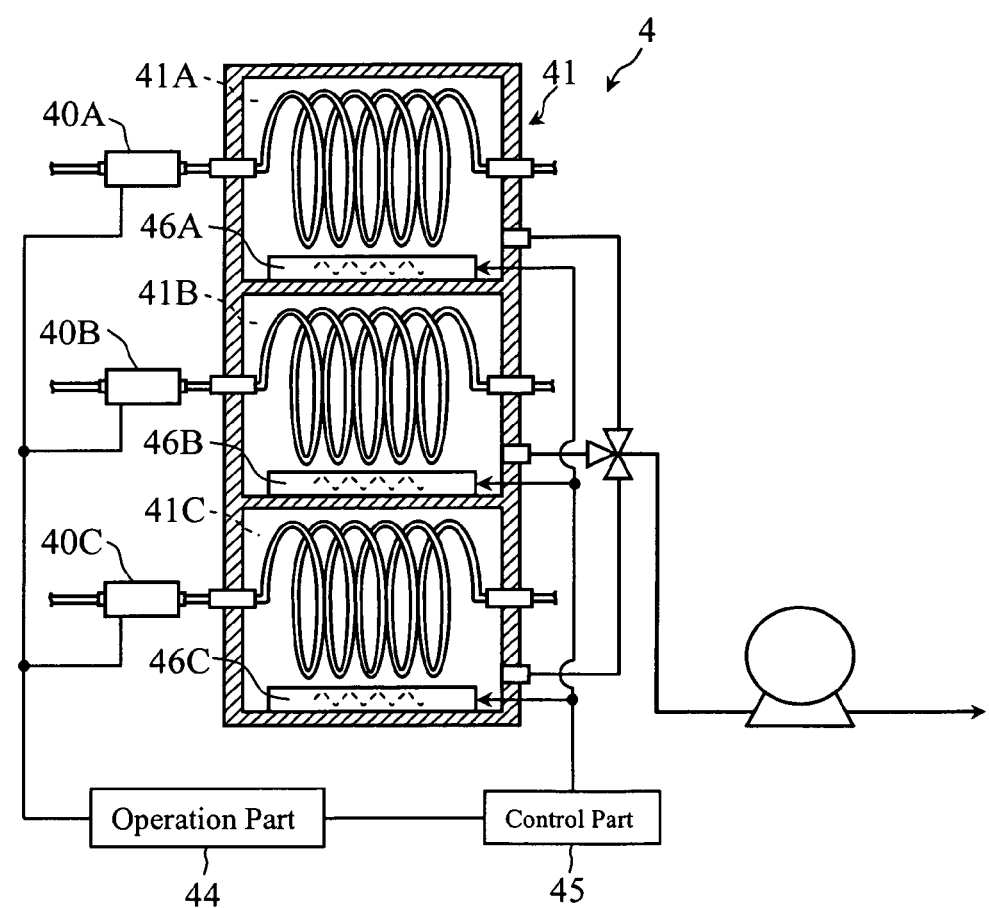
FIG. 9 is a piping diagram showing a part for explaining other example of a deaeration unit in the HPLC apparatus according to the present invention, which is equivalent to FIG. 3, in section.

In addition, as the configuration of the deaeration unit, not limited to the configuration such that the spiral tubes are contained in the decompression spaces, the configuration such that the eluting solution distribution space and the decompression space are partitioned by film-shape gas permeable film may be available. Further, it is not always necessary for the deaeration unit 4 to fix the density of the dissolved oxygen in the eluting solution by adjusting the degree of decompression of the decompression spaces 41A, 41B, and 41C, and as shown in FIG. 9, the deaeration unit 4 may be configured so that the temperatures of the decompression spaces 41A, 41B, and 41C are made constant by temperature adjusting mechanisms 46A, 46B, and 46C, and it may also be configured so that upon distribution of the eluting solution through the pipes 80A, 80B, and 80C or pipes 81A, 81B, and 81C, 84, and 85, the temperature of the eluting solution is adjusted. Further, by adjusting the feed rate of the eluting solution in accordance to the eluting solution and the environmental temperature, the density of the dissolved oxygen may be made constant by a detention time in the decompression spaces 41A, 41B, and 41C, and an oxygen partial pressure variation preventing means for preventing variation of the oxygen partial pressure in the decompression spaces 41A, 41B, and 41C may be provided.

Further, according to the present invention, the pipes 81A, 81B, and 81C are entirely formed by a material having a low permeability of an oxygen gas, however, the pipes 81A, 81B, and 81C may be partially formed by a material having a low permeability of an oxygen gas and the pipes 80A, 80B, 80C, 84, and 85 other than the pipes 81A, 81B, and 81C may be also formed by a material having a low permeability of an oxygen gas.

Figure 10:
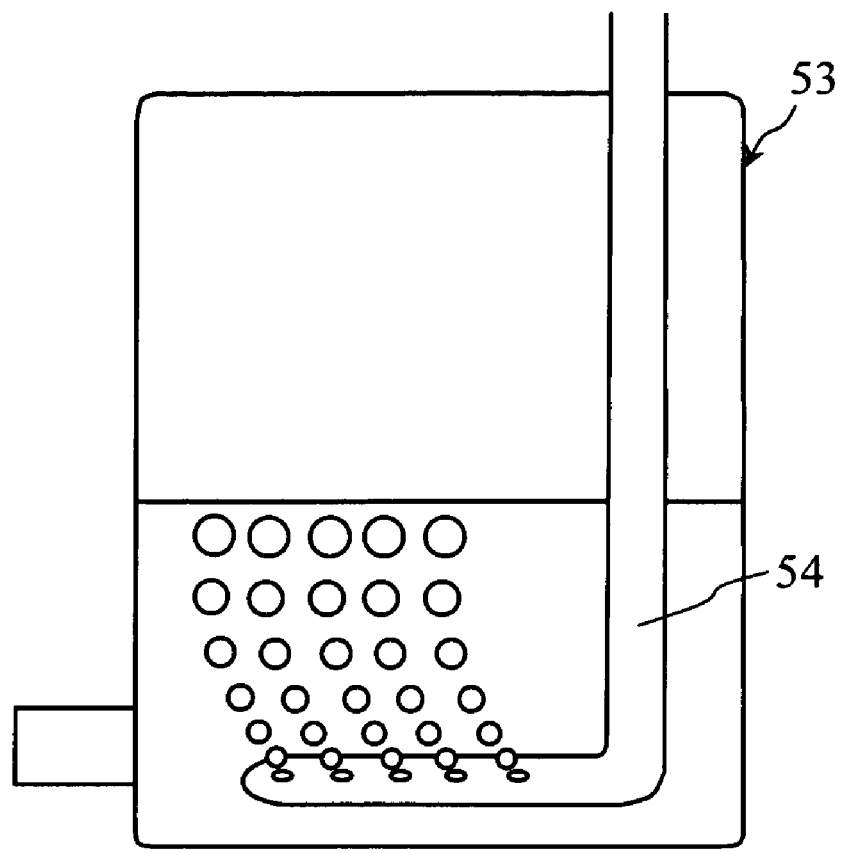
FIG. 10 is a pattern diagram showing other example of an oxygen saturation means in the HPLC apparatus according to the present invention.

In addition, as a means for improving a degree of oxygen saturation (a density of a dissolved oxygen) of a sample for introduction that is adjusted by the diluting tank 53, for example, as shown in FIG. 10, a bubbling mechanism 54 for bubbling the sample for introduction of the diluting tank 53 by an oxygen-rich gas or air may be also adopted.

Further, not limited to the HPLC apparatus for measuring a density of glycohemoglobin in blood, the present invention may be applied to the case of using a sample other than blood, the case of measuring a density of a component other than the density of glycohemoglobin, or a liquid chromatography other than the HPLC apparatus.

EXAMPLE(S)

Reference Example

According to the present reference example, a relation between an environmental temperature and a density of a dissolved oxygen was considered.

The density of the dissolved oxygen in the eluting solution to be introduced into the analysis column was measured by supplying the eluting solution as similar to a normal analysis with a dissolved oxygen density measuring apparatus connected to an entrance of a manifold in a glycohemoglobin measuring apparatus ("ADAMS A1c HA-8160", manufactured by ARKRAY, Inc.).

Using products named "61A", "61B", and "61C" (manufactured by ARKRAY, Inc.) as an eluting solution, the eluting solution was supplied so that its feed rate becomes 1.7 ml/min. An environmental temperature (a temperature of the outside of the apparatus) was set at 10° C. and 30° C. The measurement result of the density of the dissolved oxygen is shown in the following table 1.

TABLE 1

| 1 | Temperature |
| 2 | Dissolved Oxygen (mg/L) |

As seen from the table 1, at 10° C. and 30° C., a general environmental temperature range in the case of using the glycohemoglobin measuring apparatus, the density of the dissolved oxygen in the eluting solution is largely different. In other words, it seems that a ratio between oxyhemoglobin and deoxyhemoglobin in glycohemoglobin to be eluted from the analysis column is varied when the density of the dissolved oxygen in the eluting solution is varied depending on the environmental temperature. Therefore, in the case of measuring glycohemoglobin at the longest absorption wavelength of oxyhemoglobin, it seems that, when the environmental temperature is varied, even in the case of using the sample of the same density, an actual measurement value is varied.

COMPARATIVE EXAMPLE

According to the present comparative example, the influence to be given to the measurement value of glycohemoglobin by the environmental temperature was considered.

The density of glycohemoglobin was measured with respect to the case that the environmental temperature was determined to be 10° C. and 30° C. by using a glycohemoglobin measuring apparatus ("ADAMS A1c HA-8160", manufactured by ARKRAY, Inc.). As a sample, blood collected from a healthy individual (a sample of a healthy individual) and blood collected from a patient of diabetes (blood of a patient of diabetes) were used. The measurement result of glycohemoglobin is shown in the following table 2, the sample of the healthy individual is shown in FIG. 11A, and the sample of the patient of diabetes is shown in FIG. 11B, respectively.

TABLE 2

| 1 | Comparative Example |
| 2 | Density of Glycohemoglobin (%) |
| 3 | Sample of Healthy Individual |
| 4 | Sample of Patient of Diabetes |

Figure 11A:
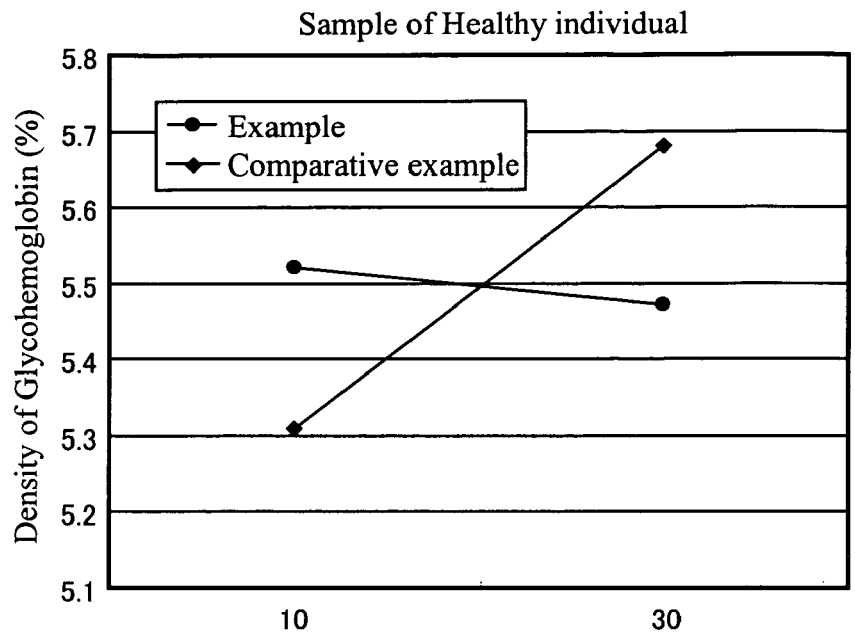
FIG. 11 is a graph showing a measurement result of a density of dissolved oxygen in an example and a comparative example.
Figure 11B:
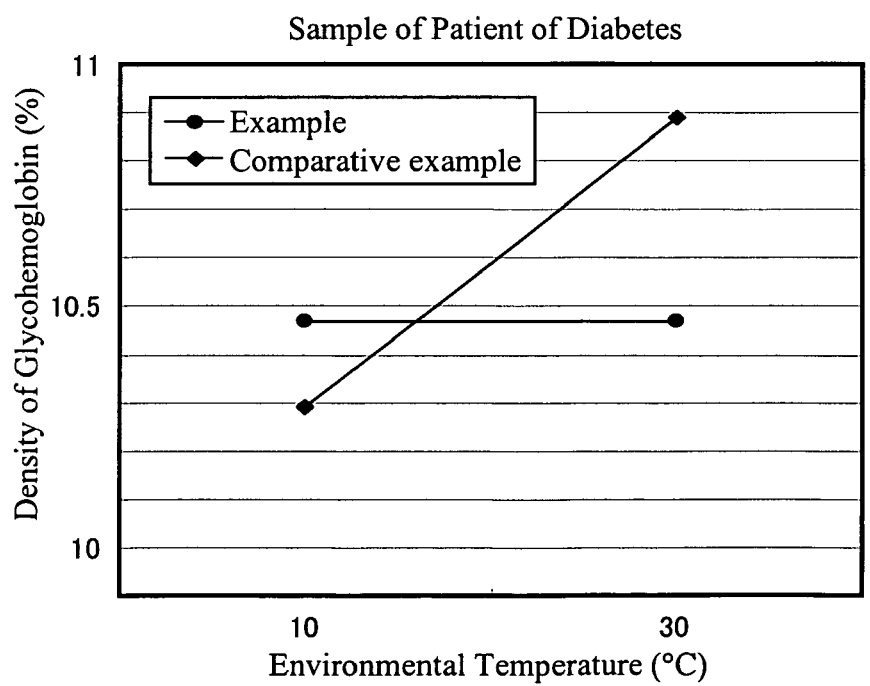

As seen from the table 2, FIG. 11A, and FIG. 11B, in the case that the environmental temperature is different, the measurement values are different both in the sample of the healthy individual and the sample of the patient of diabetes.

EXAMPLE(S)

According to the present example, an influence given to a measurement result of a density of glycohemoglobin by an environmental temperature, with respect to the case of adjusting a decompression degree in a deaerator on the basis of the temperature of the eluting solution was considered.

Glycohemoglobin is measured by using a glycohemoglobin measuring apparatus ("ADAMS A1c HA-8160", manufactured by ARKRAY, Inc.), in which a deaeration unit is configured as shown in FIG. 3 as similar to the HPLC apparatus that is previously described with reference to FIGS. 1 to 7, with a pipe to connect between the deaerator and a manifold being changed from that made of Teflon (a registered trademark) into that made of Nylon (a product name "N 2-1-1/8 (creamy white)"; manufactured by NITTA MOORE Company).

The deaeration unit was configured so as to adjust a pressure of a pump in response to the temperature of the eluting solution according to the following mathematical expression 1 by using a thermistor (a product name "PB3-43-S2"; manufactured by Shibaura Electronics Co., Ltd.) as a temperature measuring part.

Pressure $P(\text{Torr}) = -3.05T + 160$; $T=$ temperature (° C.)     [Mathematical Expression 1]

As a sample, as well as a comparative example, blood collected from a healthy individual (a sample of a healthy individual) and blood collected from a patient of diabetes (blood of a patient of diabetes) were used. The measurement result of glycohemoglobin is shown in the following table 3, the measurement result of the sample of the healthy individual is shown in FIG. 11A, and the sample of the patient of diabetes is shown in FIG. 11B, respectively.

TABLE 3

| 1 | Examples |
| 2 | Density of Glycohemoglobin (%) |
| 3 | Sample of Healthy Individual |
| 4 | Sample of Patient of Diabetes |

As seen from the table 3, FIG. 11A, and FIG. 11B, in the case of attempting to make the density of the dissolved oxygen in the eluting solution constant by adjusting the degree of decompression (the pressure of the pump) in the decompression space in response to the temperature of the eluting solution, even if the environmental temperature is different, the measurement values were substantially the same both in the sample of the healthy individual and the sample of the patient of diabetes. In other words, in the case of making the density of the dissolved oxygen in the eluting solution constant in response to the temperature of the eluting solution, or the environmental temperature, which gives an influence to the temperature of the eluting solution, with no influence of the environmental temperature or the like, it is possible to stabilize the measurement value.

Figure 12:
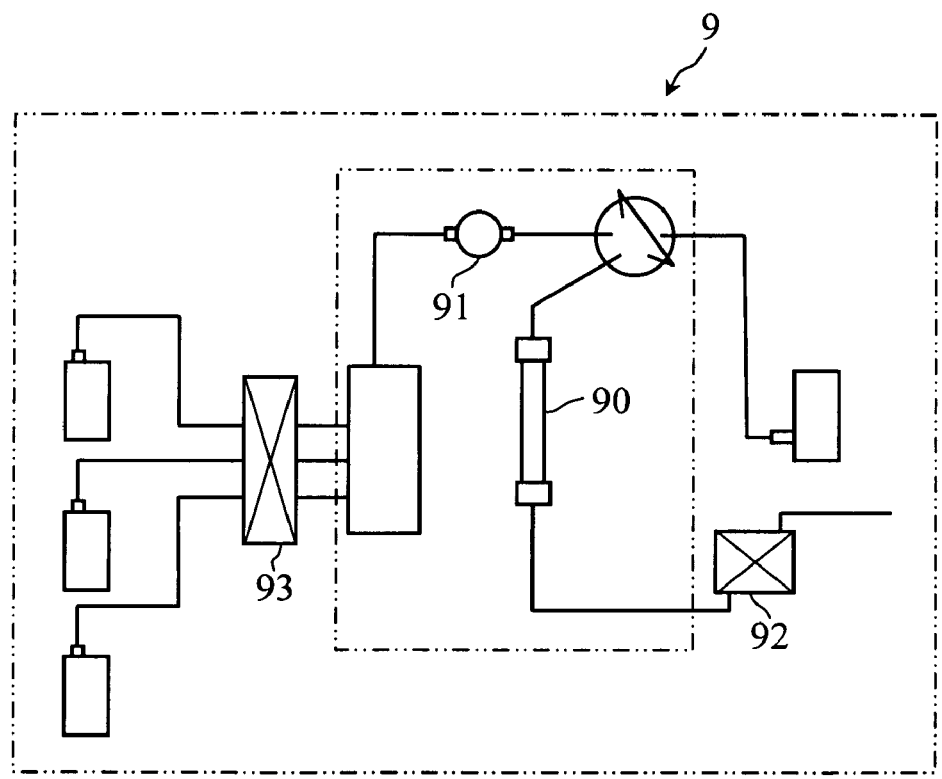
FIG. 12 is a schematic block diagram showing an example of a conventional HPLC apparatus (a high-performance liquid chromatography apparatus).
Figure 13:
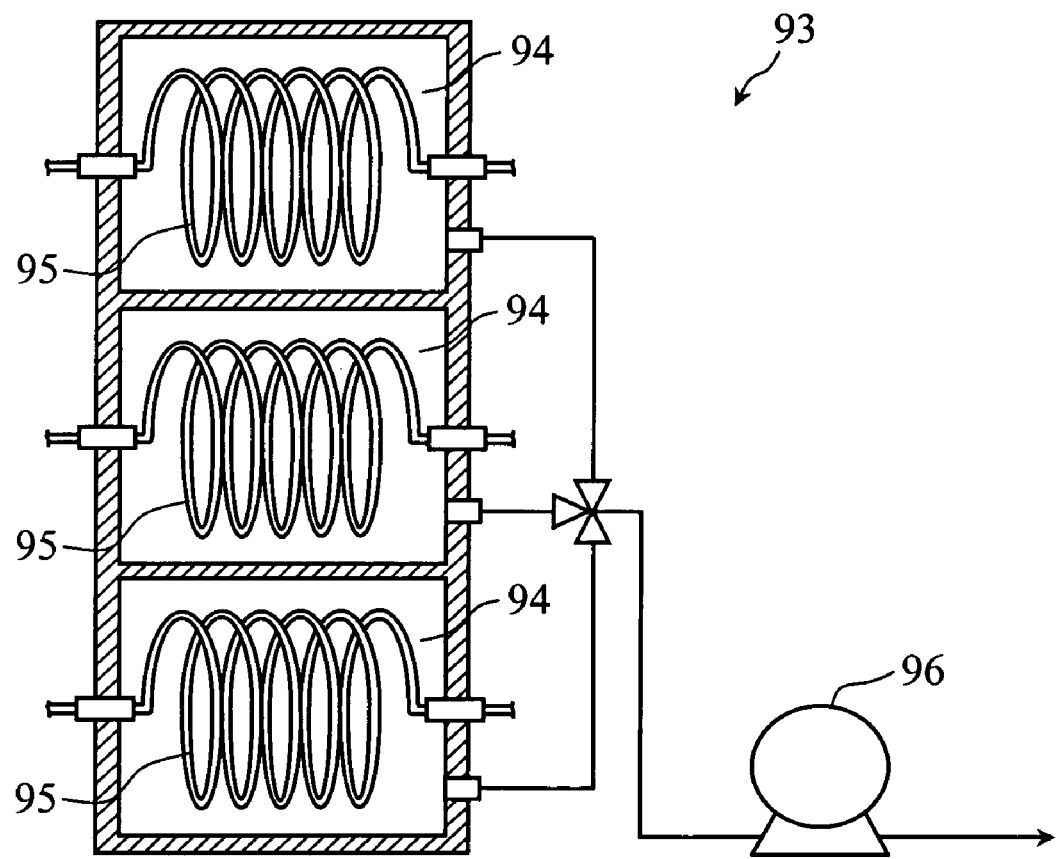
FIG. 13 is a piping diagram showing a part for explaining a deaerator in the HPLC apparatus shown in FIG. 12 in section.

FIG. 3
(1) operation part
(2) control part
FIG. 8A
(1) temperature measurement part
(2) operation part
(3) control part
FIG. 8B
(1) temperature measurement part
(2) operation part
(3) control part
FIG. 9
(1) operation part
(2) control part
FIG. 11A
(1) sample of healthy individual
(2) example, comparative example
(3) density of glycohemoglobin (%)
(4) environmental temperature (0C)
FIG. 11B
(5) sample of patient of diabetes
FIG. 12
(1) conventional art

TABLE 1

| Temperature | Dissolved oxygen (mg/L) |
|---|---|
| 10° C. | 2.07 |
| 30° C. | 1.25 |

TABLE 2

| | Density of Glycohemoglobin (%) | |
|---|---|---|
| Comparative example | 10° C. | 30° C. |
| Sample of Healthy individual | 5.31 | 5.68 |
| Sample of Patient of Diabetes | 10.29 | 10.89 |

TABLE 3

| Example | Density of Glycohemoglobin (%) | |
| --- | --- | --- |
|  | 10° C. | 30° C. |
| Sample of Healthy individual | 5.52 | 5.47 |
| Sample of Patient of Diabetes | 10.47 | 10.47 |

The invention claimed is:

1. A liquid chromatography apparatus comprising:
a column holding a column package; and
one or plural eluting solution holding parts holding an eluting solution to be supplied to the column;
wherein the liquid chromatography apparatus further comprises a dissolved oxygen density adjusting means for maintaining a density of a dissolved oxygen in the eluting solution to be supplied to the column constant,
the liquid chromatography apparatus further comprising:
a deaerator for deaerating the eluting solution during supply of the eluting solution from the eluting solution holding part to the column and having a gas permeable film and a decompression space;
wherein the dissolved oxygen density adjusting means has a temperature measuring means for directly or indirectly measuring the temperature of the eluting solution to be supplied to the column and is configured so as to adjust a density of a dissolved oxygen in the eluting solution by adjusting a degree of decompression in the decompression space based on the measurement result by the temperature measuring means.

2. The liquid chromatography apparatus according to claim 1, further comprising:
a first pipe for connecting between the eluting solution holding part and the deaerator; and
a second pipe for connecting between the deaerator and the column;
wherein the temperature measuring means is configured so as to measure the temperatures of the eluting solutions filled in the first pipe, in the second pipe, or in the deaerator, or a temperature in the decompression space.

3. The liquid chromatography apparatus according to claim 1,
wherein the temperature measuring means is configured so as to measure an environmental temperature around the liquid chromatography apparatus or a temperature in the inside of the liquid chromatography apparatus.

4. The liquid chromatography apparatus according to claim 1, further comprising:
a pipe for supplying the eluting solution from the eluting solution holding part to the column; wherein
the gas permeable film is mounted in the middle of the pipe; and
the dissolved oxygen density adjusting means has a dissolved oxygen density measuring means for measuring the density of the dissolved oxygen in the eluting solution filled in the pipe, and is configured so as to adjust a density of a dissolved oxygen in the eluting solution by adjusting a degree of decompression in the decompression space based on the measurement result by the dissolved oxygen density measuring means.

5. The liquid chromatography apparatus according to claim 4,
wherein the pipe comprises a first pipe for connecting between the eluting solution holding part and the deaerator; and
a second pipe for connecting the deaerator and the column;
wherein the dissolved oxygen density measuring means includes an oxygen sensor for measuring a density of oxygen of the eluting solutions in the first pipe, the second pipe, or the deaerator.

6. The liquid chromatography apparatus according to claim 1,
wherein the dissolved oxygen density adjusting means has a temperature adjusting mechanism for heating or cooling the eluting solution.

7. The liquid chromatography apparatus according to claim 6, further comprising:
a first pipe for connecting between the eluting solution holding part and the deaerator; and
a second pipe for connecting between the deaerator and the column;
wherein the temperature adjusting mechanism is configured so as to adjust the temperature of the eluting solution when the eluting solution passes through the first pipe, the second pipe, or the deaerator.

8. The liquid chromatography apparatus according to claim 7,
wherein the temperature adjusting mechanism is configured so as to adjust the temperature of the eluting solution based on the measurement result by the temperature measuring means.

9. The liquid chromatography apparatus according to claim 1,
wherein the liquid chromatography apparatus further comprises an oxygen partial pressure variation control means for controlling variation of the oxygen partial pressure in the decompression space.

10. The liquid chromatography apparatus according to claim 1, further comprising
a pipe for supplying the eluting solution from the eluting solution holding part to the column;
wherein the pipe has a poor oxygen permeable part, which is formed by a material having a low oxygen permeability.

11. The liquid chromatography apparatus according to claim 10,
wherein the pipe includes a first pipe for connecting between the eluting solution holding part and the deaerator; and a second pipe for connecting between the deaerator and the column; and
the poor oxygen permeable part is mounted in the entireness or a part of the second pipe.

12. The liquid chromatography apparatus according to claim 1, further comprising
a detection mechanism for detecting a specific component in a sample based on the separated liquid from the column and a pipe for connecting between the column and the detection mechanism;
wherein the pipe has a poor oxygen permeable part, which is formed by a material having a low oxygen permeability.

13. The liquid chromatography apparatus according to claim 1, further comprising
a sample adjusting means for adjusting a sample to be introduced into the column;
wherein the sample adjusting means is configured so that a degree of an oxygen saturation in the sample becomes 85% or more.

14. The liquid chromatography apparatus according to claim 13,
wherein, if a sample contains a red blood cell, the sample adjusting means is configured to dilute the sample after hemolyzing the red blood cell by using a dilute solution, and is configured so that a degree of an oxygen saturation in the sample becomes 85% or more by leaving the diluted sample for a predetermined time.

15. The liquid chromatography apparatus according to claim 14,
wherein the sample adjusting means is configured so that a degree of an oxygen saturation in the sample becomes 85% or more by opening the diluted sample to air for a predetermined time.

16. The liquid chromatography apparatus according to claim 15,
wherein the sample adjusting means is configured so that a degree of an oxygen saturation in the sample becomes 85% or more by opening the diluted sample to air for one minute or more.

17. The liquid chromatography apparatus according to claim 14,
wherein the dilute solution has a high degree of oxygen saturation, and the sample adjusting means is configured to leave the sample for a predetermined time after dilution.

18. The liquid chromatography apparatus according to claim 17,
wherein a time for leaving the sample after dilution is one minute or more.

19. The liquid chromatography apparatus according to claim 17,
wherein a solution, of which degree of oxygen saturation is 85% or more, is used as the dilute solution.

20. The liquid chromatography apparatus according to claim 13,
wherein the sample adjusting means has a bubbling mechanism for bubbling the sample by using air or oxygen-rich gas.

21. The liquid chromatography apparatus according to claim 1, further comprising
a sample adjusting means for adjusting a sample to be introduced into the column;
wherein, if the sample contains a blood cell, the sample adjusting means is configured to collect the sample for adjustment from an upper layer part of a layer containing many blood cells.

22. The liquid chromatography apparatus according to claim 21,
wherein the sample adjusting means is configured to collect a sample for adjustment from the upper layer part of the blood cell layer when separating the blood sample containing the blood cells into a red blood cell-rich blood cell layer and a red blood cell-poor blood plasma layer and to adjust a sample for introduction to be introduced into the column by using the sample for adjustment.

23. The liquid chromatography apparatus according to claim 22,
wherein the sample adjusting means comprises a detecting means for detecting an interface between the blood cell layer and the blood plasma layer; and
a sampling nozzle for collecting the sample for adjustment from the upper layer part of the blood cell layer;
wherein the sampling nozzle is configured to collect the sample for adjustment from the upper layer part of the blood cell layer based on the detection result by the detecting means.

24. The liquid chromatography apparatus according to claim 23,
wherein the sampling nozzle is configured to collect the sample for adjustment from an area, of which distance from the interface of the blood cell layer is in the range of 5 to 30% to a thickness of the blood cell layer.

25. The liquid chromatography apparatus according to claim 23,
wherein the sampling nozzle is configured to collect the sample for adjustment from an area, of which distance from the interface of the blood cell layer is in the range of 0.5 to 5.0 mm.

26. The liquid chromatography apparatus according to claim 1,
wherein the liquid chromatography apparatus is configured to measure glycohemoglobin in a sample.

27. A liquid chromatography apparatus,
wherein the liquid chromatography apparatus is configured to measure glycohemoglobin in a sample by supplying the sample and an eluting solution to a column holding a column package; the liquid chromatography apparatus comprising
a means for making a ratio between oxyhemoglobin and deoxyhemoglobin in the column constant per measurement, and
a deaerator for deaerating the eluting solution during supply of the eluting solution from an eluting solution holding part to the column and having a gas permeable film and a decompression space;
wherein the means for making a ratio between oxyhemoglobin and deoxyhemoglobin in the column constant has a temperature measuring means for directly or indirectly measuring the temperature of the eluting solution to be supplied to the column and is configured to adjust a density of a dissolved oxygen in the eluting solution by adjusting a degree of decompression in the decompression space based on the measurement result by the temperature measuring means.

* * * * *